US00PP13915P29

(12) United States Plant Patent
Whetman

(10) Patent No.: US PP13,915 P2
(45) Date of Patent: Jun. 24, 2003

(54) DIANTHUS PLANT NAMED 'VALDA ISOLDE'

(76) Inventor: John Whetman, Deer Park Farm, Chudleigh, Devon TQ13 ONH (GB)

( * ) Notice: Subject to any disclaimer, the term of this patent is extended or adjusted under 35 U.S.C. 154(b) by 0 days.

(21) Appl. No.: 10/000,726

(22) Filed: Dec. 1, 2001

(51) Int. Cl.[7] ..... A01H 5/00

(52) U.S. Cl. ..... Plt./279

(58) Field of Search ..... Plt./279, 274, 272

(56) References Cited

PUBLICATIONS

The New Royal Horticultural Society Dictionary of Gardening, vol. 2, Editor–in–Chief Anthony Huxley, The Stockton Press, New York, 1992, pp 50–56.*

EuroAmerican News, http:www.euroamprop.com/news/rhs–award.html, 2000, pp 1–3.*

* cited by examiner

*Primary Examiner*—Bruce R. Campell
*Assistant Examiner*—Anne Marie Grünberg

(57) ABSTRACT

A new cultivar of Dianthus named 'Valda Isolde' that is characterized by double, white flowers with magenta markings, a compact habit and gray-green foliage. In combination these traits set 'Valda Isolde' apart from all other existing varieties of Dianthus known to the inventor.

2 Drawing Sheets

CROSS-REFERENCES TO RELATED APPLICATIONS

The application for this new invention is co-pending with three other applications entitled 'Valda Kitty', 'Valda Louise' and 'Valda Judith'. All are derived from the same breeding program, having the same inventor and filing date as the present application entitled Dianthus 'Valda Isolde'.

Botanical classification: *Dianthus Allwoodii.*

Variety denomination: Valda Isolde.

BACKGROUND OF THE INVENTION

The present invention relates to a new and distinct cultivar of Carnation that is grown for its white flowers with magenta markings. The new cultivar is known botanically as *Dianthus Allwoodii* and will be referred to hereinafter by the cultivar name 'Valda Isolde'.

'Valda Isolde' is the product of a program conducted by the inventor in a cultivated area of Dawlish, Devon, England. The primary focus of the program was to select a variety of flower color mutations from the parent plant 'Valda Wyatt' (unpatented).

In 1995, a naturally occuring color sport mutation was found by the inventor on part of a petal of Dianthus 'Valda Wyatt' (not patented). The shoots on the lower part of the stem on which the color mutation occured were removed, rooted and grown out into flowers. One or two of the plants produced a whole flower exhibiting the mutated color. This process was repeated until a whole plant was obtained that produced the new color on all flowers.

'Valda Isolde' is a hardy perennial grown for its use as a container and landscape plant.

'Valda Isolde' was selected for its double, white flowers with magenta markings and is characterized by gray-green foliage, compact habit, profuse flowering, free flowering, long flowering and vigorous growth. It is distinguishable from the parent plant 'Valda Wyatt' by flower color. The flowers of 'Valda Wyatt' are more red (68B) with a incomplete ring (66B) around the base of the petal than those of 'Valda Isolde'.

Asexual reproduction of the new cultivar was first accomplished by the inventor who took cuttings in a cultivated area of Dawlish, Devon, England in 1995. Since that time the characteristics of the new cultivar have been determined stable and are reproduced true to type in successive generations.

SUMMARY OF THE INVENTION

The following traits have been repeatedly observed and represent the characteristics of the new cultivar. These traits in combination distinguish this cultivar from all other commercial varieties known to the inventor. 'Valda Isolde' has not been tested under all possible conditions and phenotypic differences may be observed with variations in environmental, climatic and cultural conditions.

1. Dianthus 'Valda Isolde' reaches approximately 46 cm. in height and 38 cm. in width at 12 months.
2. Dianthus 'Valda Isolde' exhibits white flowers with magenta markings.
3. Dianthus 'Valda Isolde' exhibits a compact plant habit.
4. Dianthus 'Valda Isolde' exhibits dense gray-green foliage.
5. Dianthus 'Valda Isolde' is long flowering, blooming from May to October.
6. Dianthus 'Valda Isolde' is hardy to minus 15° Centigrade.

BRIEF DESCRIPTION OF THE DRAWINGS

The accompanying drawings illustrate the distinguishing traits of the new cultivar.

The drawing on sheet 1 is a color copy of an original photograph giving a close-up view of 'Valda Isolde' and illustrating the flower color and buds.

The drawing on sheet 2 is a color copy of an original photograph illustrating the white flower of 'Valda Isolde' in comparison to the flower color of the three co-pending varieties. All drawings were made in July of plants grown in 4-inch containers out-of-doors in Encinitas, Calif. All photographs and copies were taken using conventional techniques and although colors may appear different from actual colors due to light reflectance they are as accurate as possible by conventional photography and copying.

BOTANICAL DESCRIPTION OF THE PLANT

The following is a detailed description of the new cultivar as grown in a 4-inch container out-of-doors in Arroyo Grande, Calif. The color determinations are in accordance with The Royal Horticultural Society Colour Chart of The Royal Horticultural Society, London, England, except where general color terms of ordinary dictionary significance are used.

Botanical classification: *Dianthus Allwoodii* 'Valda Isolde'.
Commercial classification: Hardy perennial.
Common name: Carnation.
Use: Container and landscape plant.
Parentage: 'Valda Isolde' is a sport of Dianthus 'Valda Wyatt' (not patented).
Plant description:
- *Bloom period.*—May to October.
- *Plant habit.*—Compact and clump forming.
- *Height.*—46 cm. in height.
- *Width.*—38 cm. in width.
- *Hardiness.*—Hardy to minus 15° Centigrade.
- *Type.*—Perennial herb.
- *Root system.*—Fibrous.
- *Propagation.*—Propagation is done by cuttings.
- *Cultural requirements.*—Plant in full sun, well-drained and moderately fertile soil.
- *Diseases and pests.*—Susceptible to known Dianthus pests and disease but no other susceptibilities are known to the inventor.
- *Time to produce rooting.*—2 weeks is required to produce roots on an initial cutting.
- *Temperature to produce rooting.*—15° Centigrade air temperature and 21° Centigrade base heat is required to produce roots on cuttings.
- *Crop time.*—5–7 months are required to produce a finished one-gallon container from a rooted cutting.

Stem:
- *Shape.*—Cylindrical.
- *Stem dimensions.*—21 cm. in length and 0.25 cm. in diameter.
- *Stem surface.*—Glabrous and glaucous.
- *Stem color.*—189A.
- *Branching.*—Numerous basal breaks.
- *Internode length.*—5–5.5 cm. between nodes.
- *Node color.*—160D.
- *Node dimensions.*—0.50 cm. in diameter and 0.50 cm. in length.

Foliage:
- *Type.*—Evergreen.
- *Shape.*—Lanceolate.
- *Division.*—Simple.
- *Apex.*—Acute.
- *Base.*—Decurrent
- *Venation.*—Not prominent.
- *Margins.*—Entire.
- *Arrangement.*—Opposite and spiraling up stem.
- *Attachment.*—Sheathing.
- *Surface (adaxial and abaxial).*—Glaucous.
- *Leaf dimensions.*—4 cm. in length and 0.25 cm. in width.
- *Leaf color (adaxial surface).*—189B.
- *Leaf color (abaxial surface).*—189A.
- *Fragrance.*—Absent.

Flowers:
- *Type.*—Salviform, double and symmetrical.
- *Flowers dimensions.*—4 cm. in length and 3.5–4 cm. in diameter including calyx.
- *Fragrance.*—Subtle clove scent.
- *Bud color.*—189A.
- *Bud shape.*—Ovate.
- *Bud dimensions.*—3.2 cm. in length and 1.25 cm. in width.
- *Petals.*—Persistent, 10–14 double petals, apopetalous, overlapping and synpetalous.
- *Petal margin.*—Crenate.
- *Petal color.*—155A with a small marking in the center that is 61A.
- *Petal shape.*—Closest to obdeltoid.
- *Petal surface.*—Glabrous.
- *Calyx dimensions.*—2.5 cm. in length and 1 cm. in diameter.
- *Calyx color.*—189A.
- *Sepals.*—Five.
- *Sepals dused or unfused.*—Fused.
- *Epicalyx.*—189A.
- *Epicalyx dimensions.*—1 cm. in length and 1 cm. in width.
- *Peduncle dimensions.*—1.3 cm. in length and 1.5 mm. in diameter.
- *Peduncle color.*—144B.
- *Lastingness of flowers.*—5 to 10 days.

Reproductive organs:
- *Stamens.*—Ten, 2 whorls, stamens of outer whorl are shorter, apostemonous, distinct, stamens evelop after pistil development, self compatible, exserted 3 mm. above corolla.
- *Stamen color.*—155A.
- *Stamen dimensions.*—2 cm. in length and 1 mm. in diameter.
- *Anther color.*—155A.
- *Anther dimensions.*—4 mm. in length and 2 mm. in diameter.
- *Anther shape.*—Oblong.
- *Anther attachment.*—*Dorsifixed.*
- *Pistil.*—One.
- *Pistil color.*—155A.
- *Pistil dimensions.*—3 cm. in length and 1 mm. in diameter.
- *Stigma.*—Two.
- *Style color.*—155A.
- *Style dimensions.*—1 cm. in length and 1 mm. in diameter and protruding 1.0–1.2 cm. above petals.
- *Ovary position.*—Superior.
- *Ovary dimensions.*—0.50 cm. in diameter and 0.75 cm. in length.
- *Ovary shape.*—Oval to round.
- *Ovary color.*—Base half is 155A and apical half is 139D.

Seed production: No seed production has been observed.

I claim:

1. A new and distinct cultivar of Dianthus plant named 'Valda Isolde' as described and illustrated herein.

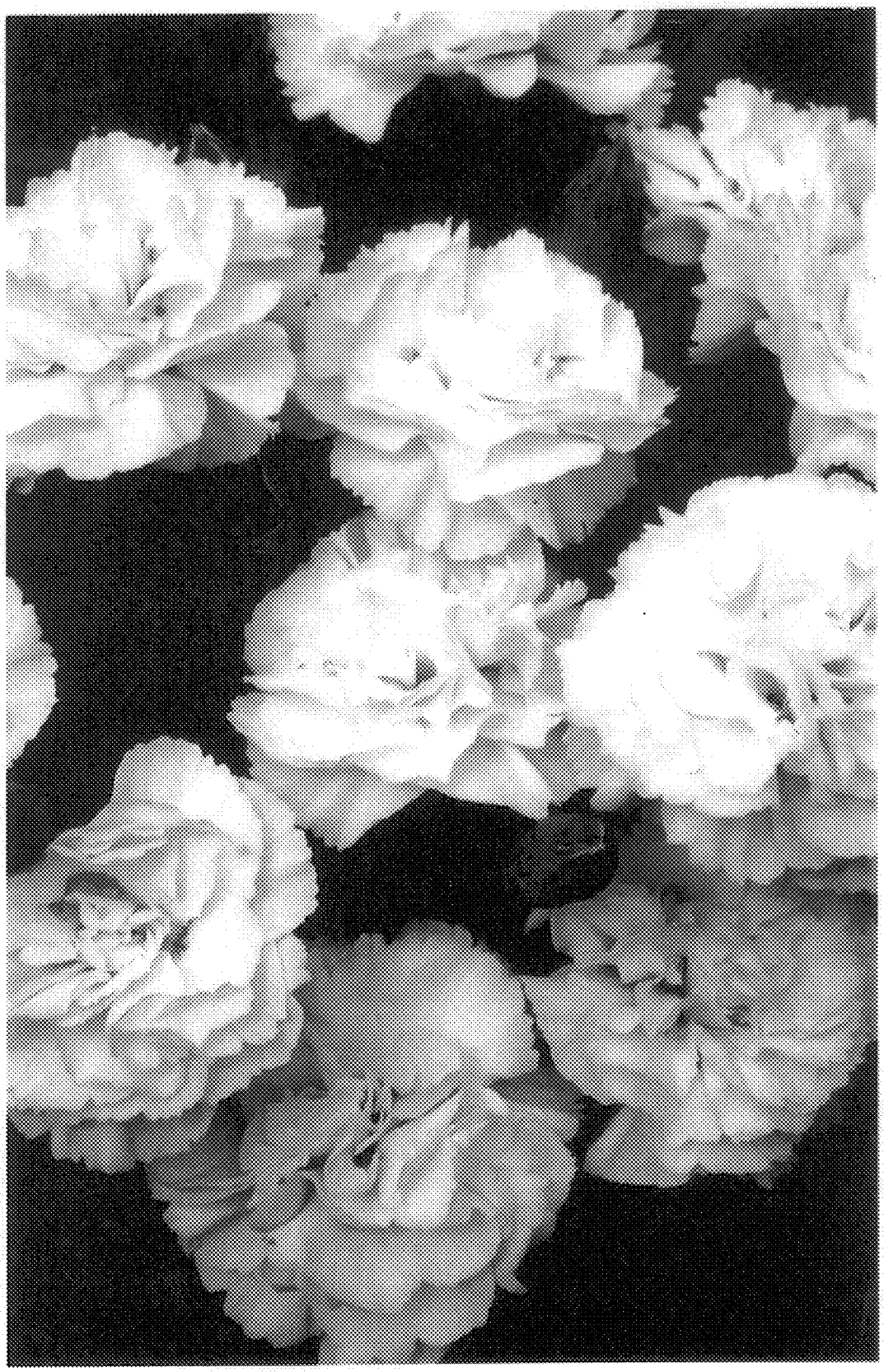

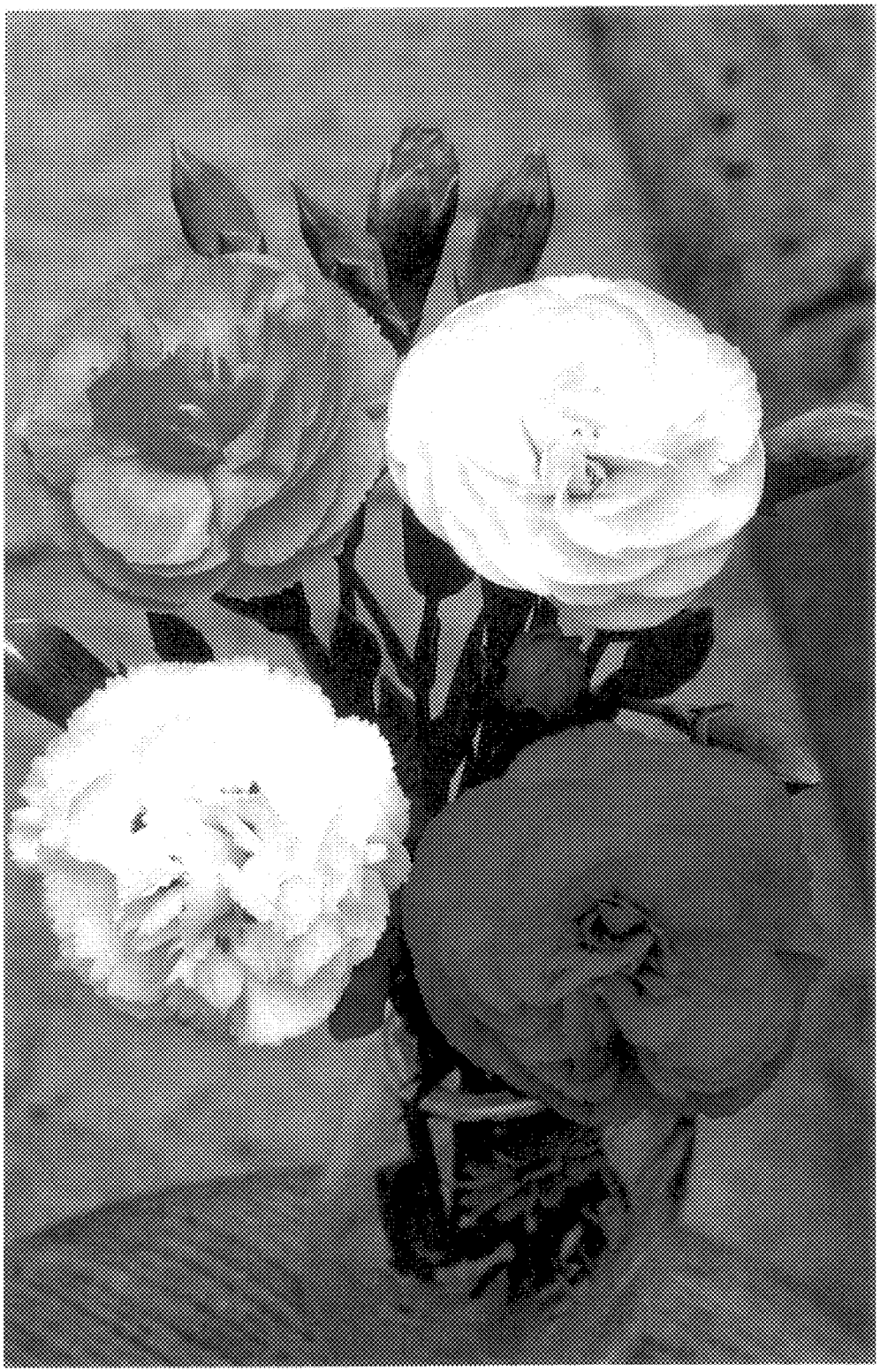

* * * * *